("12") United States Patent
Schreyer et al.

(10) Patent No.: US 10,702,620 B2
(45) Date of Patent: *Jul. 7, 2020

(54) METHOD AND APPARATUS FOR DISINFECTION OF A TEMPERATURE CONTROL DEVICE FOR HUMAN BODY TEMPERATURE CONTROL DURING EXTRACORPOREAL CIRCULATION

(71) Applicant: Sorin Group Deutschland GmbH, München (DE)

(72) Inventors: Johann Schreyer, München (DE); Erwin Knott, Poing (DE); Olivier Wolfgramm, München (DE)

(73) Assignee: LivaNova Deutschland GmbH, Munich (DE)

( * ) Notice: Subject to any disclaimer, the term of this patent is extended or adjusted under 35 U.S.C. 154(b) by 18 days.

This patent is subject to a terminal disclaimer.

(21) Appl. No.: 15/963,362

(22) Filed: Apr. 26, 2018

(65) Prior Publication Data

US 2018/0243455 A1    Aug. 30, 2018

Related U.S. Application Data

(63) Continuation of application No. 14/421,440, filed as application No. PCT/EP2013/065602 on Jul. 24, 2013, now Pat. No. 9,956,308.

(30) Foreign Application Priority Data

Aug. 13, 2012 (EP) .................................. 12180230

(51) Int. Cl.
*A61L 2/18* (2006.01)
*A61M 1/36* (2006.01)
*A61M 1/16* (2006.01)

(52) U.S. Cl.
CPC ................. *A61L 2/18* (2013.01); *A61L 2/186* (2013.01); *A61M 1/169* (2013.01);
(Continued)

(58) Field of Classification Search
CPC ........ A61L 2/18; A61L 2/186; A61L 2202/24; A61M 1/169; A61M 1/1686; A61M 1/3666; A61M 1/168; A61M 2205/366
See application file for complete search history.

(56) References Cited

U.S. PATENT DOCUMENTS 3,064,649 A    11/1962  Fuson
3,614,534 A    10/1971  Gross
(Continued)

FOREIGN PATENT DOCUMENTS

AU        07682/51 B2    12/2003
CN        1202116 A      12/1988
(Continued)

OTHER PUBLICATIONS

International Preliminary Report of Patentability issed in PCT/EP2013/065602, completed Nov. 25, 2014, 15 pages.
(Continued)

*Primary Examiner* — Regina M Yoo
(74) *Attorney, Agent, or Firm* — Faegre Drinker Biddle & Reath LLP

(57) ABSTRACT

The present application relates to a method for disinfection of a temperature control device for human body temperature control during extracorporeal circulation which temperature control is conducted by use of a heat exchanger and a temperature control liquid circulating through the heat exchanger and the temperature control device. According to the present application, the temperature control device is connected to a temperature control liquid supply and, during operation of the temperature control device for human body
(Continued)

temperature control, a disinfectant is selectively added to the temperature control liquid supply upstream of the temperature control device.

20 Claims, 1 Drawing Sheet

(52) U.S. Cl.
CPC ........ *A61M 1/1686* (2013.01); *A61M 1/3666* (2013.01); *A61L 2202/24* (2013.01); *A61M 1/168* (2013.01); *A61M 2205/366* (2013.01)

(56) References Cited

U.S. PATENT DOCUMENTS

| | | |
|---|---|---|
| 4,180,896 A | 1/1980 | Reed et al. |
| 4,221,543 A | 9/1980 | Cosentino et al. |
| 4,231,425 A | 11/1980 | Engstrom |
| 4,298,006 A | 11/1981 | Parks |
| 4,517,633 A | 5/1985 | Melcher |
| 4,966,145 A | 10/1990 | Kikumoto et al. |
| 5,019,076 A | 5/1991 | Yamanashi et al. |
| 5,117,834 A | 6/1992 | Kroll et al. |
| 5,242,404 A | 9/1993 | Conley et al. |
| 5,247,434 A * | 9/1993 | Peterson ............... A61M 1/16 210/646 |
| 5,409,612 A | 4/1995 | Maltais et al. |
| 5,487,827 A * | 1/1996 | Peterson ............... A61M 1/16 210/87 |
| 5,647,984 A * | 7/1997 | Hovland ............ A61M 1/1686 210/175 |
| 5,730,720 A | 3/1998 | Sites et al. |
| 5,863,501 A | 1/1999 | Cosentino |
| 5,871,526 A | 2/1999 | Gibbs et al. |
| 5,900,256 A | 5/1999 | Scoville et al. |
| 6,117,164 A | 9/2000 | Gildersleeve et al. |
| 6,156,007 A | 12/2000 | Ash |
| 6,175,688 B1 | 1/2001 | Cassidy et al. |
| 6,581,403 B2 | 6/2003 | Whitebook et al. |
| 6,635,076 B1 | 10/2003 | Ginsburg |
| 6,655,394 B1 | 12/2003 | Tanaka et al. |
| 6,891,136 B2 | 5/2005 | Bikovsky et al. |
| 6,939,347 B2 | 9/2005 | Thompson |
| 6,981,794 B2 | 1/2006 | Bibbo et al. |
| 7,094,231 B1 | 8/2006 | Ellman et al. |
| 7,176,419 B2 | 2/2007 | Ellis et al. |
| 7,220,260 B2 | 5/2007 | Fleming et al. |
| 7,900,629 B2 | 3/2011 | Gurnee et al. |
| 8,231,664 B2 | 7/2012 | Kulstad et al. |
| 8,308,787 B2 | 11/2012 | Kreck |
| 8,343,202 B2 | 1/2013 | Magers |
| 8,475,509 B2 | 7/2013 | Dae |
| 9,259,523 B2 * | 2/2016 | Schreyer ............... A61M 1/169 |
| 9,351,869 B2 | 5/2016 | Knott et al. |
| 9,927,416 B2 * | 3/2018 | Schreyer ............... A61M 1/169 |
| 9,956,308 B2 * | 5/2018 | Schreyer ............ A61M 1/3666 |
| 2003/0060864 A1 | 3/2003 | Whitebook et al. |
| 2004/0068310 A1 | 4/2004 | Edelman |
| 2004/0149711 A1 | 8/2004 | Wyatt et al. |
| 2004/0267340 A1 | 12/2004 | Cioanta et al. |
| 2005/0047959 A1 | 3/2005 | Brandl et al. |
| 2005/0284815 A1 | 12/2005 | Sparks et al. |
| 2007/0020142 A1 | 1/2007 | Federspiel et al. |
| 2009/0012450 A1 * | 1/2009 | Shah ............... A61L 2/183 604/29 |
| 2009/0056344 A1 | 3/2009 | Poch |
| 2009/0069731 A1 | 3/2009 | Parish et al. |
| 2010/0030306 A1 | 2/2010 | Edelman et al. |
| 2010/0106229 A1 | 4/2010 | Gammons et al. |
| 2010/0143192 A1 | 6/2010 | Myrick et al. |
| 2011/0107251 A1 | 5/2011 | Guaitoli et al. |
| 2012/0167879 A1 | 7/2012 | Bowman et al. |
| 2012/0259394 A1 | 10/2012 | Knott et al. |
| 2012/0308431 A1 * | 12/2012 | Kotsos ............... A61M 1/1686 422/3 |
| 2013/0079763 A1 | 3/2013 | Heckel et al. |
| 2013/0116761 A1 | 5/2013 | Kreck |
| 2013/0280692 A1 | 10/2013 | Gourlay |
| 2013/0324619 A1 | 12/2013 | Chtourou |
| 2013/0331739 A1 | 12/2013 | Gertner |
| 2014/0014580 A1 * | 1/2014 | Ritter ............... A61M 1/16 210/636 |
| 2014/0121734 A1 | 5/2014 | Knott et al. |
| 2014/0308654 A1 | 10/2014 | Kay et al. |
| 2015/0217014 A1 | 8/2015 | Schreyer et al. |
| 2015/0265759 A1 | 9/2015 | Schreyer et al. |
| 2016/0139100 A1 | 5/2016 | Schreyer et al. |
| 2017/0216509 A1 | 8/2017 | Bellini |
| 2017/0267907 A1 | 9/2017 | Knott et al. |
| 2018/0000634 A1 | 1/2018 | Knott et al. |

FOREIGN PATENT DOCUMENTS

| | | |
|---|---|---|
| CN | 201871012 U | 6/2011 |
| CN | 202154894 U | 3/2012 |
| CN | 102526822 A | 7/2012 |
| DE | 3883452 T2 | 1/1994 |
| DE | 19531935 A1 | 2/1997 |
| DE | 19924856 A1 | 12/2000 |
| DE | 69331840 T2 | 11/2002 |
| DE | 69634572 T2 | 2/2006 |
| EP | 0297723 A2 | 1/1989 |
| EP | 1267958 A2 | 1/2003 |
| EP | 1970080 A1 | 9/2008 |
| EP | 2698176 A1 | 2/2014 |
| EP | 2698177 B1 | 1/2015 |
| FR | 2631241 A1 | 11/1989 |
| JP | 54154195 A | 12/1979 |
| JP | 61131753 A | 6/1986 |
| JP | H1157733 A | 3/1999 |
| JP | 2001506971 A | 5/2001 |
| JP | 2002539893 A | 11/2002 |
| JP | 2003260131 A | 9/2003 |
| JP | 2005074236 A | 3/2005 |
| JP | 2005-514085 A | 5/2005 |
| JP | 2005219041 A | 8/2005 |
| JP | 2008111612 A | 5/2008 |
| JP | 2014503305 A | 2/2014 |
| WO | 97/06840 A1 | 2/1997 |
| WO | 01/72352 A2 | 10/2001 |
| WO | 03/54660 A2 | 7/2003 |
| WO | 2006/063080 A1 | 6/2006 |
| WO | 2009094601 A2 | 7/2009 |
| WO | 2014/026833 A1 | 2/2014 |

OTHER PUBLICATIONS

International Preliminary Report on Patentability issued in PCT/EP2013/065601, completed Feb. 25, 2014, 7 pages.
International Preliminary Report on Patentability issued in PCT/EP2014/067746, dated Mar. 2, 2017, 7 pages.
International Search Report and Written Opinion issued in PCT/EP2013/065602, dated Sep. 24, 2013, 8 pages.
International Search Report and Written Opinion issued in PCT/EP2014/067746, dated Dec. 1, 2014, 8 pages.
International Search Report and Written Opinion issued in PCT/EP2013/065601, dated Sep. 26, 2013, 9 pages.
European Search Report and Search Opinion Received for EP Application No. 12180230.0, dated Nov. 20, 2012, 5 pages.

* cited by examiner

METHOD AND APPARATUS FOR DISINFECTION OF A TEMPERATURE CONTROL DEVICE FOR HUMAN BODY TEMPERATURE CONTROL DURING EXTRACORPOREAL CIRCULATION

CROSS-REFERENCE TO RELATED APPLICATIONS

This application is a continuation of U.S. application Ser. No. 14/421,440, filed Feb. 12, 2015, which is a national phase application of PCT Application No. PCT/EP2013/065602, internationally filed Jul. 24, 2013, which claims priority to European Application No. 12 180 230.0, filed Aug. 13, 2012, all of which are herein incorporated by reference in their entirety.

TECHNICAL FIELD

The present invention relates to a method for disinfection of a temperature control device, namely a heater and/or cooler system, for human body temperature control during extracorporeal circulation which temperature control is conducted by use of a heat exchanger and a temperature control liquid circulating through the heat exchanger and the temperature control device and a corresponding heat exchanging system.

BACKGROUND

Extracorporeal circulation of blood is used in certain surgical procedures such as during heart surgery. During the extracorporeal circulation, the body temperature of the patient can be controlled, by controlling the temperature of the blood during extracorporeal circulation. For this purpose, a patient temperature control system can be provided by means of which the temperature of the blood of the patient in the circulation can be raised or lowered. The blood thus controlled, flows through the patient and the body of the patient approaches the temperature of the blood. So as to heat or cool the blood, the temperature control system comprises a heater and/or cooler device providing a liquid circulation to a disposable (single use) heat exchanger that transfers energy to and/or away from the patient's blood circulation. The liquid can be water. The heat exchanger for the blood is a strict dual circuit system/ the blood side and the liquid side being separated from each other so that any mixture, such as by means of diffusion, between the blood in one of the circuits and the temperature control liquid in the other of the circuits is inhibited as much as possible. Nevertheless, care has to be taken to avoid health risks stemming from the liquid.

SUMMARY OF INVENTION

The applicant has designed a mobile temperature control device for human body temperature control during extracorporeal circulation. Such a mobile device can be connected to a circuit of temperature control liquid to be used in a heat exchanger. The mobile temperature control device preferably is provided with exchangeable hoses or tubes or other conduits. Further, connecting and disconnecting these conduits can more easily be achieved if the conduits are not filled with the temperature control liquid during connecting and disconnecting. Likewise, it is preferred if the circuit can be emptied of temperature control liquid for the connection and disconnection of the mobile temperature control device. The preferred mobile device is consequently provided with an open reservoir where the temperature control liquid is exposed to environmental air. The temperature control liquid can be fed into the circuit from this reservoir and can be returned to it. Any air which might be trapped in one of the conduits during connecting or disconnecting the conduit and the temperature control device or the heat exchanger can be bled to the environment via the open reservoir. This means, however, that the temperature control liquid is exposed to the air of the environment. Substances used as temperature control liquid, in particular water, are prone to microbial contamination when exposed to environmental air. If the temperature control liquid was exposed to the environmental air, disinfecting the temperature control device and the temperature control liquid can then improve the microbial status of the liquid and render the mobile device maintenance- and service-friendly. It is usually necessary to manually conduct regular disinfection procedures on the heater or cooler for the heat exchanger which are very time consuming and thus expensive.

The present invention addresses the necessity for regular manual disinfection procedures of the temperature control device for the above-identified technical field. Overcoming this necessity would result in an improved efficiency of the temperature control device and the disinfection of a temperature control device.

A heat exchanger for the human body temperature control using a temperature control device according to the present invention comprises a blood side circulating blood and a temperature control liquid side circulating a temperature control liquid, wherein heat can be exchanged between the temperature control liquid on the temperature control liquid side and the blood on the blood side. In the heat exchanger, the blood side and the temperature control liquid side are strictly separated from each other. The heat exchanger itself is a single-use device. After the operation of the patient, the heat exchanger is disposed. However, the temperature control device is a multi-use device and must be maintained in a disinfected state. The temperature control liquid side of the heat exchanger is connected to a temperature control device for the temperature of the temperature control liquid to be efficiently and reliably controlled. The temperature control device is a device which is configured for heating and/or cooling the temperature control liquid to be introduced into the heat exchanger for human body temperature control during extracorporeal circulation.

According to the inventive method for disinfection of such a temperature control device for human body temperature control during extracorporeal circulation, the temperature control device is connected to a temperature control liquid supply and, during operation of the temperature control device for human body temperature control, a disinfectant is selectively added to the temperature control liquid supply upstream of the temperature control device. By connecting the temperature control device to a temperature control liquid supply, temperature control liquid cannot only circulate in a closed loop system, but additional temperature control liquid can be added to the temperature control device and, thus, also to the temperature control liquid side of the heat exchanger. By selectively adding disinfectant to the temperature control liquid supply upstream of the heater or cooler, i. e. the temperature control device, the disinfectant can effectively be added into the temperature control device and therefore disinfect the temperature control device during operation for human body temperature control. This overcomes the necessity of an interruption of the use of the temperature control device which to date implies disconnecting the temperature control device from the circulation system and disinfecting it remotely. Accordingly, the invention makes disinfecting the temperature control device much more efficient. The temperature control liquid supply can selectively supply additional temperature control liquid to the temperature control device and preferably, if additional temperature control liquid is supplied, excessive temperature control liquid is released from the temperature control device.

In connection with the present invention the term human means mammal or human and animal. It is to be noted that the inventive disinfection method is completely conducted outside of the human or animal body. Preferably, the addition of the disinfectant is controlled by a computer. The use of a computer facilitates automation of the disinfection for it to be semi-automatic or fully automatic. This automation includes dosing of disinfectant or mixing of several disinfectants to be added to the temperature control liquid. Such a computer preferably comprises a user interface by which a user can set the desired concentration and choice of disinfectants to be added to the temperature control liquid. Further, it is possible that the computer controls fully-automatic disinfection, in particular if a sensor, such as a Clark sensor, is provided which measures the concentration of disinfectant in the temperature control fluid in the circuit. The information from this sensor can be used by the computer for fully automatically controlling a method for disinfecting or maintaining a disinfection status of a circuit for extracorporeal circulation including the devices being part of this circuit such as a heat exchanger and a temperature control device. In particular, the disinfectant comprises at least one of sodium hypochlorite, hydrogen peroxide and citric acid. These disinfection agents can be added to the temperature control liquid either alone or in combination with each other and further disinfectants. Use of one of these preferred disinfectants ensures that disinfection can be conducted during operation of the temperature control device for human body temperature control. The preferred disinfectants are, under certain conditions in particular, in specific ranges of concentration, not harmful to the human body, if the temperature control liquid should leak into the blood of the patient via the heat exchanger or directly from the temperature control device or a connection tube, so that these disinfectants can, in moderate concentrations, be used while the blood circulation takes place. A disinfectant in connection with the described invention is a disinfecting substance which can be, and preferably is, permanently present in the temperature control liquid without being hazardous to the patient during extracorporeal circulation and without damaging a (plastic) heat exchanger or other part of the circuit for extracorporeal circulation. As long as the concentration of the disinfecting substance in the temperature control liquid is above a certain minimum concentration/ the substance is considered a disinfecting substance as the circuit is then in a disinfected state. The disinfectant could also be called a "long term disinfectant" and can optionally be defined by a maximum concentration in the temperature control liquid. "Long term" is an individual period of time without a precise minimum or maximum. Any disinfectant which, in its specific concentration in the temperature control liquid, can be used during the extracorporeal circulation and which does not require the circulation to be stopped for it being used for disinfection without being hazardous to the patient and without damaging the heat exchanger or any other part of the circuit for extracorporeal circulation is considered a long term disinfectant in the sense of the present application. A preferable concentration of such disinfectant is below 500 mg/l, more preferably 300 mg/l or below but advantageously 100 mg/l or above and/more preferably 200 mg/l or above/or combinations of these ranges.

Preferably, the disinfectant is added by use of at least one electronically controlled liquid valve. Such a liquid valve enables an automation device such as a computer to control the addition of disinfectant autonomously. Particularly the temperature control liquid includes water and preferably consists of water 1 the long term disinfectant and unavoidable contaminants. Since water is usually ready available in the required quality and quantity in many places, using water as the temperature control liquid is preferred. In the present text, the term "water" means "drinking water". This implies a standardized quality and cleanliness of the water which is sufficient for using the water as temperature control liquid in a heat exchanger and a corresponding temperature control device for human body temperature control during extracorporeal circulation. Further, water is compatible with many long term disinfectants and, hence, allows for choosing the disinfectant from a large group of potential long term disinfectants. However, also other substances which differ from water can be used as temperature control liquid. An inventive heat exchanging system for human body temperature control during extracorporeal circulation comprises the temperature control device described above and a disinfecting device connected to the temperature control device on an upstream side thereof via a temperature control liquid supply. This disinfecting device is configured for selectively adding a long term disinfectant to the temperature control liquid supply during operation of the temperature control device for human body temperature control. The disinfecting device can preferably be a dedicated separate apparatus which can be connected to the temperature control liquid supply, for example fresh water supply, as well as to the waste liquid sink, for example waste water sink. Alternatively, the disinfecting device can also be integrally formed with the temperature control device. In particular/ the disinfecting device comprises a computer controlling the addition of disinfectant to the temperature control liquid. This computer is preferably provided with a user interface in order to set desired properties for the addition of disinfectant to the temperature control liquid. The computer can preferably control an electronic valve in order to control the addition of disinfectant. Further preferred is if the disinfecting device comprises more than one electronically controlled liquid valves in order to control the addition of a mixture of several disinfectants to the temperature control liquid. The long term disinfectant preferably comprises one of sodium hypochlorite, hydrogen peroxide and citric acid as mentioned before and, as is further preferred, the disinfecting device may comprise several containers, each for one of a respective long term disinfectant so that the disinfectants can be mixed in the disinfecting device and added to the temperature control liquid as a mixture. Such a mixture can be tailored to the required disinfection procedure applied to the temperature control device. According to a preferred embodiment, the heat exchanging system is configured for conducting the inventive method described before and defined in the claims. Reference is made to the co-assigned patent application EP 12 180 231.8 filed on Aug. 13, 2012, entitled "Method for controlling a disinfection status of a temperature control device for human body temperature control during extracorporeal circulation", the complete content of which is hereby incorporated herein. The co-assigned patent application describes and claims a method for controlling a disinfection status of a temperature control device for human body temperature control during extracorporeal circulation which uses a long term disinfectant. The method and the device described in the coassigned patent application can preferably be combined with the invention described in the present application, in particular in that the addition of disinfectant to the temperature control liquid described in the present application can be based on the method and device disclosed in the co-assigned patent application. In other words, the method and device disclosed in the co-assigned patent application can be combined with the invention disclosed in the present application. This particularly facilitates performing a fully-automatic or at least semi-automatic disinfection method based on the information obtained by the method and/or device of the co-assigned application. In particular, the outcome of the method for controlling the disinfection status of a temperature control device of the co-assigned application can be that the disinfection status of the temperature control device is insufficient. In this case, the method of disinfection as described in the present application can be used for improving the disinfection status of the temperature control device, preferably semiautomatically or fully-automatically.

DETAILED DESCRIPTION

Figure 1:
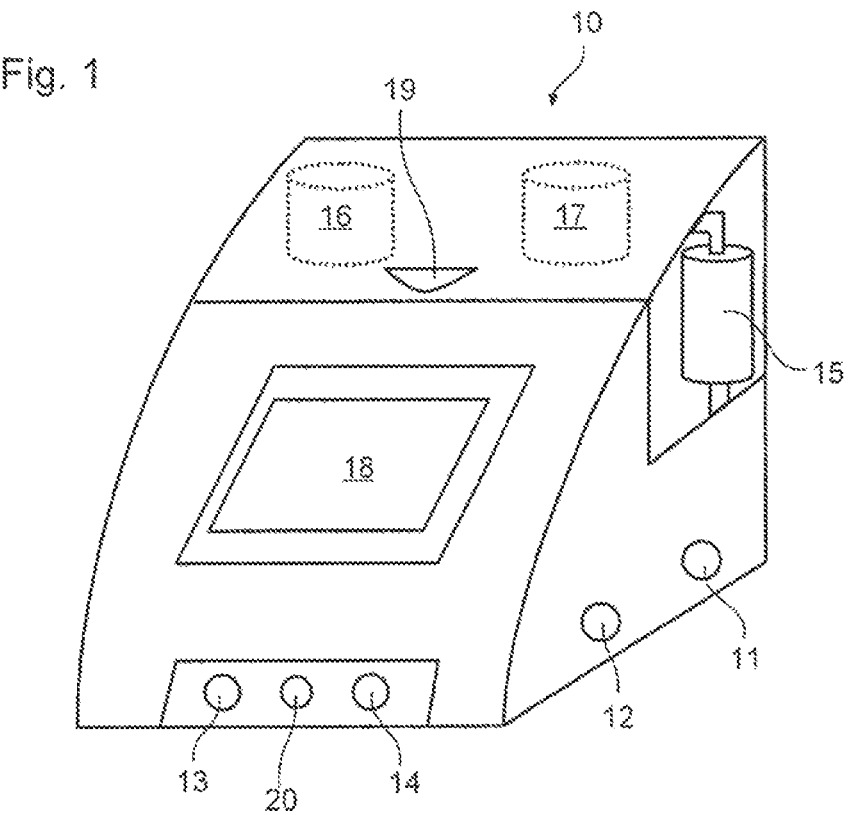
FIG. 1 shows a schematic view of the disinfecting device for a preferred heat exchanging system.

FIG. 1 shows a schematic illustration of a disinfecting device 10 for a heat exchanging system. The disinfecting device 10 comprises a tap water supply 11 and a waste water drain 12 for connecting the disinfecting device 10 to an external supply/sink of temperature control liquid, in this case water. The disinfecting device 10 further comprises a heater and/or cooler supply 13 and a heater and/or cooler drain 14 through which the disinfecting device 10 can be connected to a temperature control device, namely a heater and/or cooler (not illustrated). The illustrated embodiment comprises one set of supply 13 and drain 14 for either a heater or a cooler; if a heater and a cooler is to be used, then the device may comprise a single set or two sets. The water supplied via the tap water supply 11 is guided through a filter system 15 in order to further clean the water supplied to the disinfecting device 10. The disinfecting device 10 further comprises a first disinfectant container 16 and a second disinfectant container 17 which contain different long term disinfecting agents such as sodium hypochlorite, hydrogen peroxide or citric acid for decalcification. The disinfecting agents of these containers 16, 17 can selectively be mixed and added to the water supplied to the disinfecting device 10 through the tap water supply 11. The mixture of the disinfecting agent and the tap water can then be circulated through the heater and/or cooler supply 13 into the heater and/or cooler. The disinfecting device 10 further comprises a control display 18 by which a user can influence the setting for the disinfection procedure conducted by the disinfecting device 10. For the user to be able to remotely control the disinfecting device 10, the disinfecting device further comprises a remote control terminal 20 through which a remote control can be connected to the disinfecting device 10. In order to facilitate refilling or exchanging the disinfectant containers 16, 17, the disinfecting device 10 is provided with a housing having an opening which is normally closed by a lid 19. Opening the lid allows for accessing the interior of the housing of the disinfecting device 10 and either refilling the disinfectant containers or exchanging them.

Figure 2:
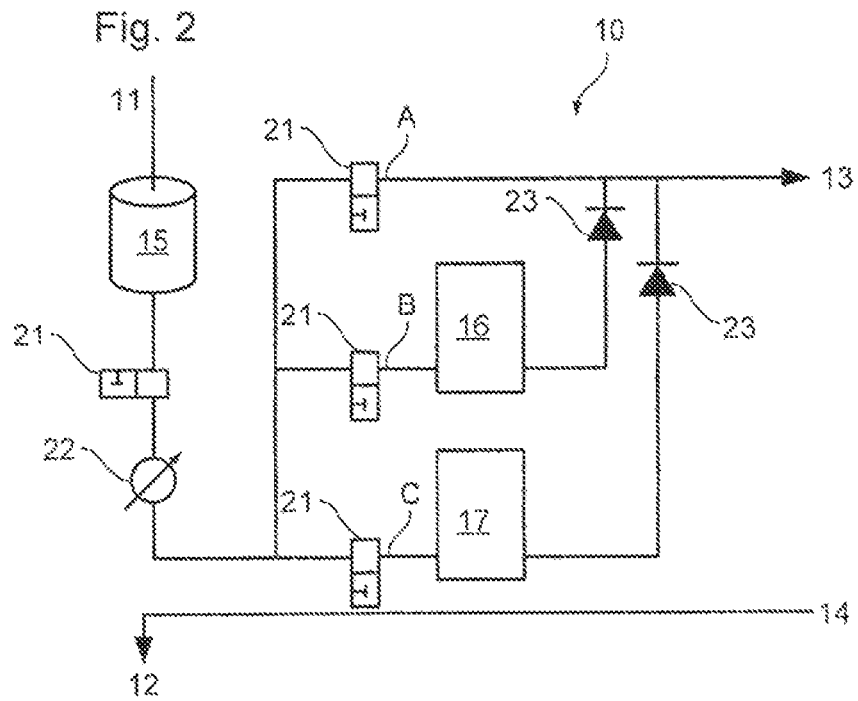
FIG. 2 illustrates the function of a preferred disinfecting device for a preferred heat exchanging system.

FIG. 2 illustrates the function and operation of the disinfecting device shown in FIG. 1 and like elements of the disinfecting device 10 in FIG. 1 are assigned like reference signs also in the schematic view of FIG. 2. The tap water supplied via the tap water supply 11 is led through the filter 15 and through a first control valve 21. A flow meter 22 indicates the liquid flow into the disinfecting device 10. Behind the flow meter 22, the duct guiding the water through the disinfecting device 10 continues into three parallel ducts, each provided with flow control valves 21. A first duct A passes water through the disinfecting device 10 directly to the heater or cooler supply terminal 13 so that no disinfectant is added to the water. A second duct B passes water through the first disinfectant container 16 by means of which a first disinfecting agent, e.g. sodium hypochlorite, is added to the water. The water can be passed through a portion of the container 16 which contains a predetermined amount of the first disinfecting agent of a predetermined concentration. The water passing through the first disinfectant container 16 then includes the disinfecting agent. Alternatively, the disinfecting agent can be injected into the water passing through the first disinfectant container 16 so that the water obtains a predetermined concentration of a predetermined first disinfecting agent. Behind the first disinfectant container 16, a return valve 23 allows for letting the water including disinfectant flow to the heater and/or cooler via the heater and/or cooler supply terminal 13 but prevents any backflow reversely into the second duct B. A third duct C having basically the same structure as the second duct B is provided for the second disinfectant container 17 comprising e.g. hydrogen peroxide. The design of ducts A, B and C permits, depending on the water flow control valves 21, to either bypass water past the disinfectant containers 16, 17 and thus to add pure water, i.e. water in the same quality and composition as supplied via the tap water supply, to the heater and/or cooler, or to selectively pass the supplied water through one or both of the disinfectant containers 16, 17 containing different disinfectants in order to add one disinfectant or a mixture of the two disinfectants to the water to be supplied to the heater and/or cooler. Naturally, the invention is not limited to the preferred embodiments described before and in particular the number of disinfectant containers and ducts in the disinfecting device can be chosen in accordance with the necessary supply water treatment.

We claim:

1. A method for disinfection of a temperature control device for human body temperature control during extracorporeal circulation, the method comprising:
    conducting temperature control by use of a heat exchanger and a temperature control liquid circulating through the heat exchanger and the temperature control device; and
    adding a disinfectant to the temperature control liquid upstream of the temperature control device during operation of the temperature control device.

2. The method of claim 1, wherein adding a disinfectant to the temperature control liquid includes passing the temperature control liquid through a container having a predetermined amount of disinfectant at a predetermined concentration.

3. The method of claim 1, wherein adding a disinfectant to the temperature control liquid includes passing a first portion of the temperature control liquid through a first container and passing a second portion of the temperature control liquid through a second container.

4. The method of claim 1, wherein adding a disinfectant to the temperature control liquid includes injecting the disinfectant into the temperature control liquid that is passing through a container to obtain a predetermined concentration of the disinfectant in the temperature control liquid.

5. The method of claim 1, wherein adding a disinfectant to the temperature control liquid includes controlling, by a computer, the addition of the disinfectant to the temperature control liquid.

6. The method of claim 1, wherein adding a disinfectant to the temperature control liquid includes using at least one electronically controlled liquid valve.

7. The method of claim 1, wherein the disinfectant comprises at least one of sodium hypochlorite, hydrogen peroxide and citric acid.

8. The method of claim 1, wherein the temperature control liquid includes water, the disinfectant, and unavoidable contaminants.

9. A method for disinfection of a temperature control device for human body temperature control during extracorporeal circulation, the method comprising:
    circulating a temperature control liquid through a heat exchanger and the temperature control device to control temperature of the temperature control liquid;
    passing the temperature control liquid through at least one container during operation of the temperature control device for human body temperature control; and
    adding a disinfectant to the temperature control liquid upstream of the temperature control device during operation of the temperature control device for human body temperature control.

10. The method of claim 9, wherein passing the temperature control liquid through at least one container includes passing the temperature control liquid through a disinfectant container having a predetermined amount of disinfectant at a predetermined concentration.

11. The method of claim 9, wherein passing the temperature control liquid through at least one container includes passing a first portion of the temperature control liquid through a first container having a predetermined amount of a first disinfectant at a predetermined concentration and passing a second portion of the temperature control liquid through a second container having a predetermined amount of a second disinfectant at a predetermined concentration.

12. The method of claim 9, wherein adding a disinfectant to the temperature control liquid includes injecting the disinfectant into the temperature control liquid that is passing through the at least one container to obtain a predetermined concentration of the disinfectant in the temperature control liquid.

13. A heat exchanging system for human body temperature control during extracorporeal circulation, comprising:
    a temperature control device configured for heating or cooling a temperature control liquid to be circulated through a temperature control liquid side of a heat exchanger for conducting the human body temperature control; and
    a disinfecting device connected to the temperature control device, the disinfecting device configured to selectively add a disinfectant to the temperature control liquid during operation of the temperature control device for human body temperature control.

14. The heat exchanging system of claim 13, comprising a disinfectant container having a predetermined amount of disinfectant at a predetermined concentration, wherein the disinfecting device is configured to pass the temperature control liquid through the disinfectant container.

15. The heat exchanging system of claim 13, comprising a container configured to have disinfectant added to the container to provide a predetermined concentration of the disinfectant in the temperature control liquid that is passing through the container.

16. The heat exchanging system of claim 13, wherein the disinfecting device is connected to the temperature control device on an upstream side of the temperature control device.

17. The heat exchanging system of claim 13, wherein the disinfecting device comprises at least one of a control display by which a user can control settings of a disinfection procedure conducted by the disinfecting device, and a remote control terminal by which a user can remotely control settings of a disinfection procedure conducted by the disinfecting device.

18. The heat exchanging system of claim 13, wherein the disinfecting device comprises a computer controlling the addition of the disinfectant to the temperature control liquid.

19. The heat exchanging system of claim 13, further comprising at least one electronically controlled liquid valve configured for adding the disinfectant to the temperature control liquid.

20. The heat exchanging system of claim 13, wherein the temperature control liquid includes water, disinfectant, and unavoidable contaminants.

* * * * *